United States Patent
Huang

(10) Patent No.: US 6,206,270 B1
(45) Date of Patent: Mar. 27, 2001

(54) METHOD OF ASSEMBLING NEEDLES FOR EYEBROW MAKEUP

(76) Inventor: Te Shih Huang, 3 Fl., No., 19, Alley 2, Lane 283, Chung-Shan Road, Sec. 1, Pan-Chiao City, Taipei County (TW)

(*) Notice: Subject to any disclaimer, the term of this patent is extended or adjusted under 35 U.S.C. 154(b) by 0 days.

(21) Appl. No.: 09/476,718

(22) Filed: Dec. 30, 1999

(51) Int. Cl.$^7$ .................................................. B23K 31/02
(52) U.S. Cl. ........................... 228/138; 228/212; 81/9.22; 604/47; 604/48
(58) Field of Search .................................... 228/135, 138, 228/175, 212, 44.3, 49.1; 132/216, 218; 81/9.22; 604/47, 48, 173; 606/116

(56) References Cited

U.S. PATENT DOCUMENTS

| | | | |
|---|---|---|---|
| 3,685,101 | * | 8/1972 | Egerer .................................. 19/129 R |
| 3,872,730 | * | 3/1975 | Ringrose et al. .................. 73/864.23 |
| 3,987,839 | * | 10/1976 | Pace ......................................... 163/5 |
| 4,230,001 | * | 10/1980 | Noll et al. .............................. 81/9.22 |
| 4,377,897 | * | 3/1983 | Eichenbaum et al. ................. 29/516 |
| 4,574,716 | * | 3/1986 | Czelusniak, Jr. .................. 112/80.45 |
| 4,798,582 | * | 1/1989 | Sarath et al. ........................... 604/47 |
| 4,862,772 | * | 9/1989 | Piperato ................................ 81/9.22 |
| 5,632,437 | * | 5/1997 | Vongfuangfoo et al. ............. 228/177 |
| 5,988,174 | * | 11/1999 | Chasan ................................. 128/898 |

FOREIGN PATENT DOCUMENTS 304872   5/1997  (TW) .

\* cited by examiner

*Primary Examiner*—Samuel M. Heinrich
(74) *Attorney, Agent, or Firm*—Ware, Fressola, Van Der Sluys & Adolphson LLP

(57) ABSTRACT

A method of assembling needles for eyebrow makeup comprises the steps of inserting short needles into holes, wrapping a thermoplastic tube onto distal ends of short needles, inserting a long needle through thermoplastic tube and one hole such that sharp points of the needles contact top surface of planar heat-proof plate, moving needles and fastener plate assembly into oven to heat for integrally forming a needle assembly, taking needle assembly and fastener plate assembly from oven, removing needle assembly from the fastener plate assembly, inserting needle assembly into a hole through a tapered portion of fastener body for compressing the sharp ends of needles, and soldering needles together form a complete needle assembly.

5 Claims, 5 Drawing Sheets

METHOD OF ASSEMBLING NEEDLES FOR EYEBROW MAKEUP

BACKGROUND OF THE INVENTION

1. Field of the Invention

The present invention relates to a needle, and more particularly to a method of assembling needles for eyebrow makeup.

2. Description of Related Art

A conventional method of assembling needles for eyebrow makeup is shown in FIG. 5 characterized in that a plurality of needles (two are shown in which one is a long needle) are joined together by solder. In detail, two needles are laid side by side on a plane without employing any fastener. together to join the short needle and long needle. But this is unsatisfactory for the following reasons:

1) The soldering process is time consuming because the needles are not easily aligned.
2) Even aligned needles are susceptible to misaligment of out of alignment when soldering, resulting in a misaligned needle assembly product which in turn adversely affects the success of eyebrow makeup. In other words, an uneven eyebrow makeup is possible by this needle assembly.

Another conventional method of assembling needles for eyebrow makeup is shown in FIG. 6 characterized in that a plurality of needles (two are shown in which one is a long needle) are joined together by a short stainless steel tube. In detail, two needles are laid side by side on a plane (i.e., aligned). A short stainless steel tube is wrapped onto the join of short needle and long needle. Then a force is applied by a machine on a suitable position of the tube to press a circumferential recess thereon for securing the needle assembly. But this is unsatisfactory for the following reasons:

1) The force applying process may needlessly cause the aligned needles to become misaligned resulting in misaligned needle assembly product which in turn adversely affects the success of eyebrow makeup. In other words, an uneven eyebrow makeup is possible by this needle assembly.
2) Such needle assembly is not capable of fastening needles tightly when the needle assembly consists of more than three needles.

A Taiwanese Pat. Publication No. 304,872 discloses a method of assembling needles for eyebrow makeup wherein a plurality of holes with different diameters are provided on a copper base, and a copper tube is put on the base for serving as a securing means to fasten needles. But this is unsatisfactory for the following reasons.

1) It is not easy to drill holes on the copper base and copper tube, resulting in a consumption of time. Further, copper base is bulky and susceptible to oxidation.
2) The base and tube, after heated by oven, are not capable of being processed immediately by hand because to they are hot, resulting in a prolongation of time to fabricate the needle assembly.
3) The patent employs a quick adhesive in place of above solder and stainless steel tube for fastening needle assembly. However, the quick adhesive is easily penetrated into the space between needle assembly and the internal surface of copper tube as well as the space between the external surface of copper tube and copper base due to a capillary attraction that exists in the holes of copper base, resulting in immediately taking needle assembly from the holes impossible. This adversely affects the process of fabricating needle assembly.
4) Such needle assembly easily becomes loose in a relatively high vibration environment.
5) The quick adhesive is dissolved when temperature of process reaches 80° C. or above.

Thus, it is desirable to provide an improved method of assembling needles for eyebrow makeup in order to overcome the above drawbacks of prior art.

SUMMARY OF THE INVENTION

It is an object of the present invention to provide a method of assembling needles for eyebrow makeup in a system including a heat-proof plate having a plurality of holes, a planar heat-proof plate with the heat-proof plate placed thereon, and a fixture for fixing heat-proof plate and planar heat-proof plate together on the four comers thereof to form a fastener plate assembly, the method comprising the steps of inserting at least one short needle into one of the holes, wrapping a thermoplastic tube onto the distal end of the short needle, inserting a long needle through the thermoplastic tube and hole such that the sharp points of needles contact the top surface of planar heat-proof plate, moving the attached needles and fastener plate assembly into an oven to heat for contracting the thermoplastic tube onto the needles for integrally forming a needle assembly, taking the attached needle assembly and fastener plate assembly from the oven, removing the needle assembly from the fastener plate assembly, inserting the needle assembly into a hole through a top of tapered portion of fastener body for compressing the sharp points of needles, soldering needles together in a suitable position between thermoplastic tube and fastener body to form a complete needle assembly.

The advantages offered by the present invention are as follows:

1) The sharp ends of needles are flush, resulting in a possibility of fully automatic process which in turn increases yield.
2) Human errors are reduced, saving time, and reducing costs.
3) Fastener plate assembly and fastener body are easily manufactured, and are light weight, stainless, and reusable.
4) Fastener plate assembly is heat-proof such that it is capable of being processed immediately by hand after being heated by oven, resulting in a reduction of time of fabricating needle assembly.
5) High quality and safe.

The above and other objects, features and advantages of the present invention will become apparent from the following detailed description taken with the accompanying drawings.

DETAILED DESCRIPTION OF THE PREFERRED EMBODIMENTS

Figure 1:
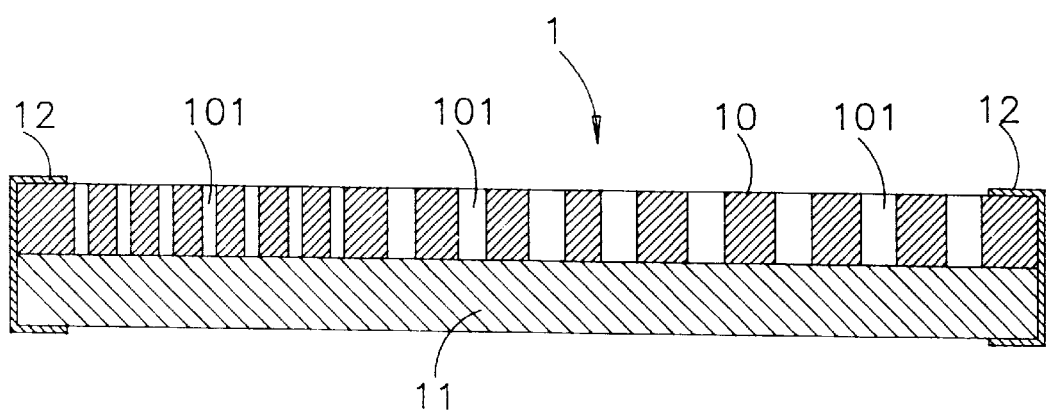
FIG. 1 is a sectional view of fastener plate assembly of a preferred embodiment of the present invention.
Figures 2A, 2B:
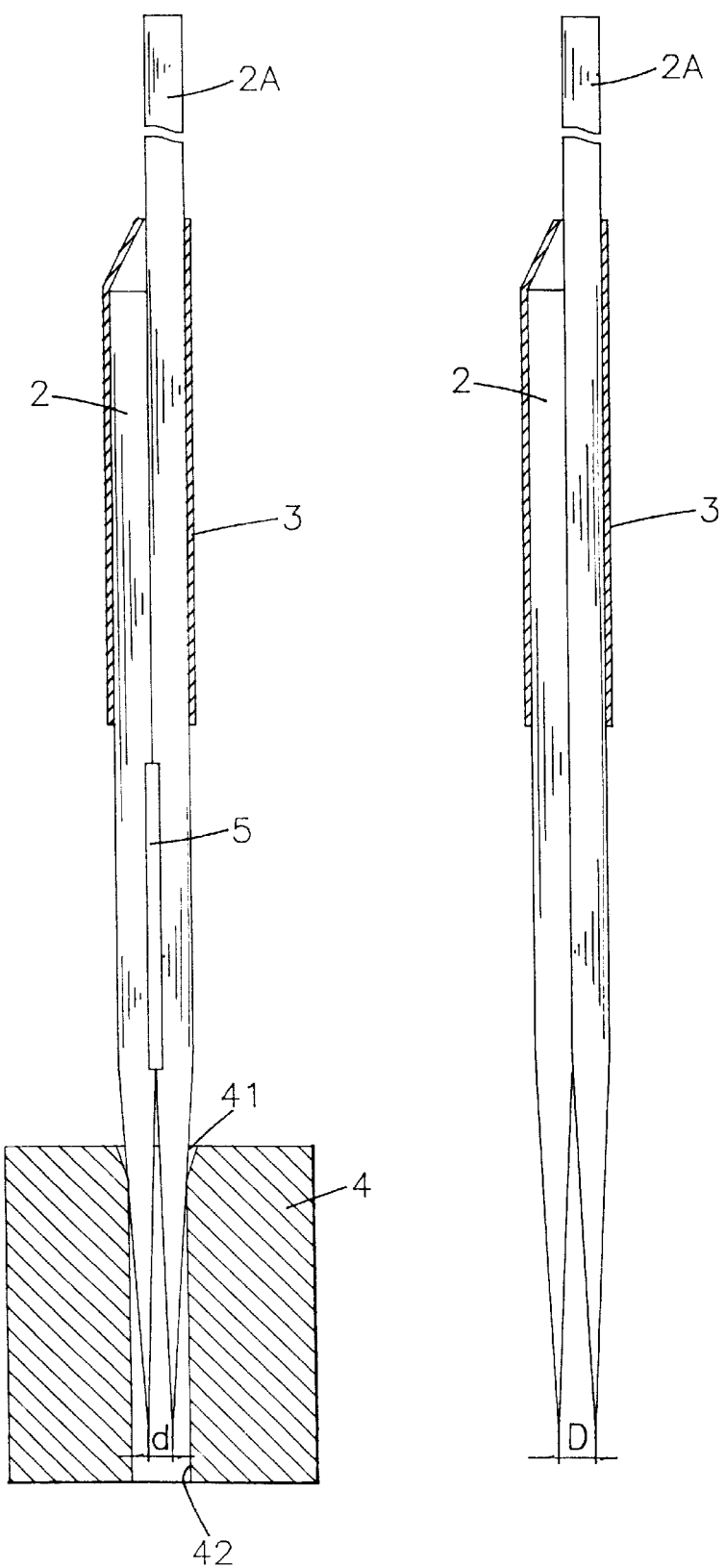
FIGS. 2A and 2B are sectional views illustrating before and after needle assembly of the present invention is fastened respectively.

Referring to FIGS. 1–2, there is shown a method of assembling needles for eyebrow makeup in a system comprising a heat-proof plate 10 (e.g., a bakelite or the like) of a generally rectangular body having a plurality of holes 101 penetrating from top to bottom, a planar heat-proof plate 11 (e.g., a glass or the like) having the same size as the heat-proof plate 10 with the heat-proof plate 10 placed thereon, and a fixture 12 for fixing heat-proof plate 10 and planar heat-proof plate 11 together on the four corners thereof to form a fastener plate assembly 1. The method comprises the steps of inserting at least one short needle 2 (only one short needle is shown in FIG. 2) into hole 101 to keep it upright, wrapping a thermoplastic tube 3 onto the distal end (i.e., not the end with a sharp point) of short needle 2, and inserting a long needle 2A through the thermoplastic tube 3 and hole 101 such that the sharp points of needles 2 and 2A both contact the top surface of planar heat-proof plate 11. The method also comprises the steps of moving the attached needles 2 and 2A and fastener plate assembly 1 into an oven (not shown) to heat shrink the thermoplastic tube 3 onto the needles 2 and 2A for integrally forming a needle assembly, taking the attached needle assembly and fastener plate assembly 1 from the oven, removing the needle assembly from the fastener plate assembly 1, and inserting the needle assembly into a hole 42 through a top of tapered portion 41 of fastener body 4 for shaping therein. Note that the distance between the two sharp points (i.e., d in FIG. 2B) is smaller than that of D in FIG. 2A. In other words, a compaction of needles 2 and 2A is carried out by the fastener body 4. Last, needles 2 and 2A are soldered together in a suitable position between thermoplastic tube 3 and fastener body 4 to form a soldered portion 5.

Figure 3A:
FIGS. 3A–3C are top views illustrating various configurations of needle assembly before being fastened respectively.
Figure 3B:
Figure 3C:
Figure 4A:
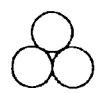
FIGS. 4A–4C are top views illustrating various configurations of needle assembly of FIGS. 3A–3C after being fastened respectively.
Figure 4B:
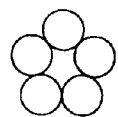
Figure 4C:
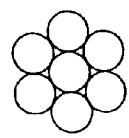
Figure 5:
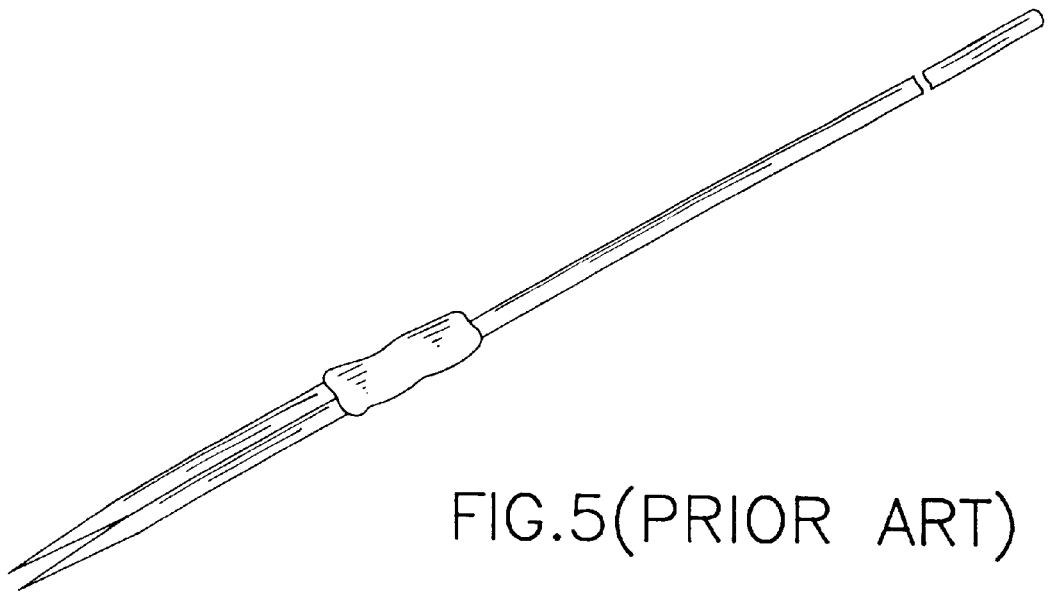
FIG. 5 is a perspective view of a first prior art needle assembly.
Figure 6:
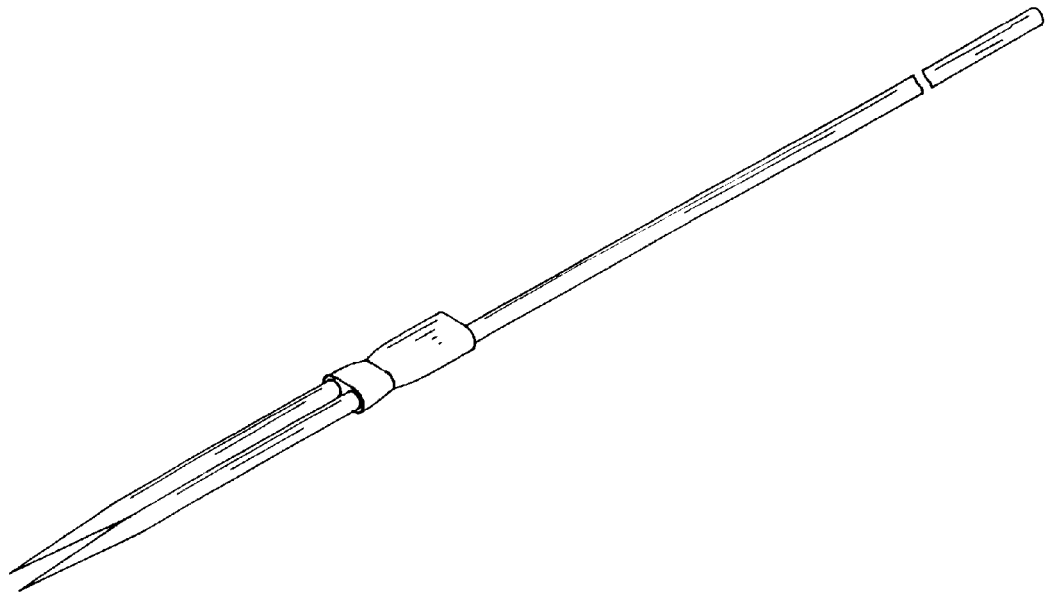
FIG. 6 is a perspective view of a second prior art needle assembly.

FIGS. 3A–3C are top views illustrating needle assemblies consisting of three, five, and seven needles before being fastened by fastener body 4 and soldered respectively, while FIGS. 4A–4C are top views illustrating needle assemblies of FIGS. 3A–3C after being fastened by fastener body 4 and soldered respectively In comparison of FIGS. 3A–3C with FIGS. 4A–4C, it is found that needle assemblies in the former have a loose irregular configuration, while needle assemblies in the later have a much compact configuration as well as a flush needle points. Thus a successful eyebrow makeup is carried out by the present invention.

While the invention herein disclosed has been described by means of specific embodiments, numerous modifications and variations could be made thereto by those skilled in the art without departing from the scope of the invention set forth in the claims.

What is claimed is:

1. A method of assembling needles for eyebrow makeup in a system, the method comprising the steps of:
    a) providing a heat-proof plate having a plurality of holes;
    b) providing a planar heat-proof plate;
    c) placing the heat-proof plate on the planar heat-proof plate;
    d) providing a fixture for fixing the heat-proof plate and the planar heat-proof plate together to form a fastener plate assembly;
    e) inserting at least one short needle having a sharp point and a distal end into a hole in the heat-proof plate;
    f) wrapping a thermoplatic tube onto the distal end of the short needles;
    g) inserting a long needle having a sharp point through the thermoplastic tube and the hold in the heat-proof plate such that the sharp points of the long and short needles contact the top surface of the planar heat-proof plate;
    h) moving the needles and the fastener plate assembly into an oven to heat shrink the thermoplastic tube onto the needles to integrally form a needle assembly having a first diameter;
    i) taking the needle assembly and the fastener plate assembly from the oven;
    j) removing the needle assembly from the fastener plate assembly;
    k) inserting the needle assembly into a hole of a fastener body through a top of a tapered portion of the fastener body for compressing the sharp points of the needles, wherein the hole of the fastener body has a second diameter small than the first diameter; and
    l) soldering the needles together in a suitable position between the thermoplastic tube and the fastener body to form a complete needle assembly.

2. The method of claim 1, wherein the heat-proof plate is made of a heat-proof material.

3. The method of claim 2, wherein the heat-proof material is a bakelite.

4. The method of claim 1, wherein the planar heat-proof plate is made of a heat-proof material.

5. The method of claim 4, wherein the heat-proof material is a glass.

* * * * *

UNITED STATES PATENT AND TRADEMARK OFFICE
CERTIFICATE OF CORRECTION

PATENT NO. : 6,206,270 B1
DATED : March 27, 2001
INVENTOR(S) : Huang

It is certified that error appears in the above-identified patent and that said Letters Patent is hereby corrected as shown below:

Column 1,
Line 16, please replace "." with -- and then soldered --.
Line 21, "out of alignment" should be deleted.
Line 57, "to" should be deleted.

Column 3,
Line 46, after "respectively", -- . -- should be inserted.

Signed and Sealed this

Eleventh Day of September, 2001

*Attest:*

*Attesting Officer*

NICHOLAS P. GODICI
*Acting Director of the United States Patent and Trademark Office*